United States Patent [19]

Krámer et al.

[11] Patent Number: 4,851,405
[45] Date of Patent: Jul. 25, 1989

[54] AMINOMETHYL HETEROCYCLIC COMPOUNDS

[75] Inventors: Wolfgang Krámer, Burscheid; Joachim Weissmüller, Monheim; Dieter Berg, Wuppertal; Stefan Dutzmann, Duesseldorf, all of Fed. Rep. of Germany

[73] Assignee: Bayer Aktiengesellschaft, Leverkusen, Fed. Rep. of Germany

[21] Appl. No.: 161,830

[22] Filed: Feb. 29, 1988

[30] Foreign Application Priority Data

Mar. 7, 1987 [DE] Fed. Rep. of Germany ....... 3707364
Oct. 21, 1987 [DE] Fed. Rep. of Germany ....... 3735555

[51] Int. Cl.$^4$ .................. A01N 43/28; C07D 327/04; C07D 317/28; C07D 405/06
[52] U.S. Cl. .................... 514/212; 514/462; 514/227.8; 514/731.5; 514/278; 514/409; 549/30; 549/341; 549/342; 548/407; 548/209; 544/60; 544/70; 546/15; 540/543
[58] Field of Search ............ 514/439, 462, 227.8, 514/231.5, 278, 409, 212; 549/30, 341, 342; 548/407; 544/60, 70; 546/15; 540/543

[56] References Cited

U.S. PATENT DOCUMENTS

| | | | |
|---|---|---|---|
| 2,606,909 | 8/1952 | Blicke | 544/70 |
| 3,022,222 | 2/1962 | Hennis | 549/341 |
| 3,025,214 | 3/1962 | Bath | 549/30 |
| 3,641,039 | 2/1972 | Rakoczi et al. | 546/19 |
| 4,503,059 | 3/1985 | Kramer et al. | 514/231.5 |
| 4,542,130 | 9/1985 | Weissmuller et al. | 549/30 |
| 4,713,379 | 12/1987 | Kramer et al. | 514/212 |

FOREIGN PATENT DOCUMENTS

| | | | |
|---|---|---|---|
| 0097822 | 1/1984 | European Pat. Off. | |
| 1965321 | 9/1970 | Fed. Rep. of Germany | |
| 2215205 | 9/1974 | France | 514/462 |

OTHER PUBLICATIONS

Chemical Abstracts, Band 90, 2/26/79, Wolinski, Jerzy . . . Search for Anticholinegic Compounds.
Chemical Abstracts Band 88, 1/2/78.
Chemical Abstracts, Band 87, 11/21/77.
Chemical Abstracts, Band 70, 3/31/69.
Chemical Abstracts, Band 91 , 7/30/79, and Chemical Abstracts, Band 101, 10/22/84.

Primary Examiner—Mary C. Lee
Assistant Examiner—John A. A. Russell
Attorney, Agent, or Firm—Sprung, Horn, Kramer & Woods

[57] ABSTRACT

Fungicidally effective aminomethyl heterocyclic compounds of the formula

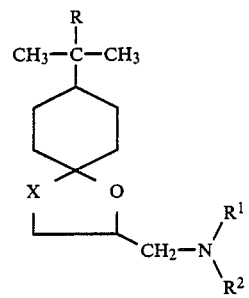

in which
X represents oxygen or sulphur,
R represents hydrogen or alkyl, or represents in each case optionally substituted cyclohexyl or phenyl and
$R^1$ and $R^2$ independently of one another each represent hydrogen, alkyl, alkenyl, alkinyl, alkoxyalkyl, dialkoxyalkyl, hydroalkyl, hydroxyalkoxyalkyl, alkoxycarbonylalkyl, dioxolanylalkyl, dioxanylalkyl or oxolanylalkyl, or represent in each case optionally substituted cycloalkylalkyl, cycloalkyl, aralkyl, aralkenyl or aryl, or
$R^1$ and $R^2$, together with the nitrogen atom to which they are bonded, represent an optionally substituted saturated heterocyclic radical, which can optionally contain further hetero atoms,
or acid addition salts thereof.

11 Claims, No Drawings

AMINOMETHYL HETEROCYCLIC COMPOUNDS

The invention relates to new aminomethyl heterocyclic compounds, several processes for their preparation and their use as agents for combating pests.

It is already known that certain aminomethyldioxolanes, such as, for example, 3-isobutyl-2-methyl-3-(1-piperidinylmethyl)-dioxolane or 2-methyl-2-nonyl-4-di-n-butylaminomethyldioxolane have fungicidal properties (compare European Patent No. 97,822).

However, the efficacy of these already known compounds is not completely satisfactory in all fields of use, especially when low amounts are applied and in the case of low concentrations.

New aminomethyl heterocyclic compounds of the general formula (I)

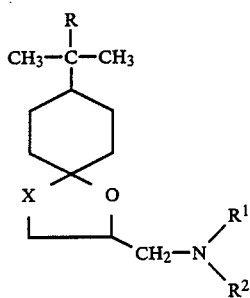
(I)

in which

X represents oxygen or sulphur,

R represents hydrogen or alkyl, or represents in each case optionally substituted cyclohexyl or phenyl and $R^1$ and $R^2$ independently of one another each represent hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl or represent in each case optionally substituted cycloalkylalkyl, cycloalkyl, aralkyl, aralkenyl or aryl, or $R^1$ and $R^2$, together with the nitrogen atom to which they are bonded, represent an optionally substituted saturated heterocyclic radical, which can optionally contain further hetero atoms, and acid addition salts thereof which are tolerated by plants, have been found.

The compounds of the formula (I) can be in the form of geometric and/or optical isomers or isomer mixtures of varying composition. Both the pure isomers and the isomer mixtures are claimed according to the invention.

It has furthermore been found that the new aminomethyl heterocyclic compounds of the general formula (I)

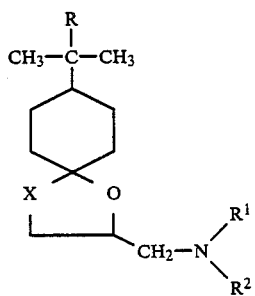
(I)

in which

X represents oxygen or sulphur,

R represents hydrogen or alkyl, or represents in each case optionally substituted cyclohexyl or phenyl and $R^1$ and $R^2$ independently of one another each represent hydrogen, alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl, or oxolanylalkyl, or represent in each case optionally substituted cycloalkylalkyl, cycloalkyl, aralkyl, aralkenyl, or aryl, or $R^1$ and $R^2$, together with the nitrogen atom to which they are bonded, represent an optionally substituted saturated heterocyclic radical, which can optionally contain further hetero atoms, and acid addition salts thereof which are tolerated by plants, are obtained by a process in which (a) substituted heterocyclic compounds of the formula (II)

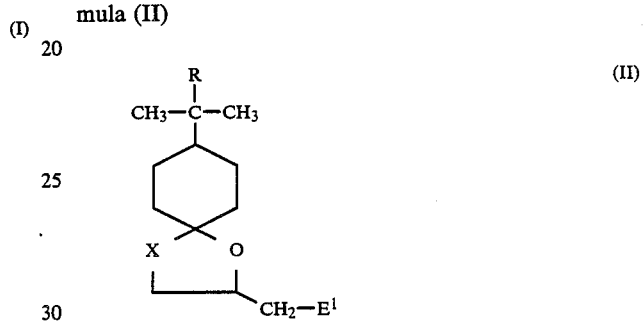
(II)

in which

R and X have the abovementioned meaning and $E^1$ represents an electron-withdrawing leaving group, are reacted with amines of the formula (III)

(III)

in which $R^1$ and $R^2$ have the abovementioned meaning, if appropriate in the presence of a diluent and if appropriate in the presence of an acid-binding agent, or by a process in which (b) the aminomethyl heterocyclic compounds obtainable by process (a), of the formula (Ia)

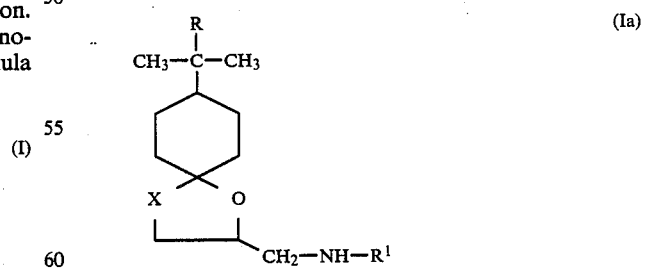
(Ia)

in which

R, $R^1$ and X have the abovementioned meaning, are reacted with alkylating agents of the formula (IV)

(IV)

in which $R^{2-1}$ represents alkyl, alkenyl, alkinyl, alkoxyalkyl, dialkoxyalkyl, hydroxyalkyl, hydroxyalkoxyalkyl, alkoxycarbonylalkyl, dioxolanylalkyl, dioxanylalkyl or oxolanylalkyl, or represents in each case optionally substituted cycloalkylalkyl, cycloalkyl, aralkyl or aralkenyl and $E^2$ represents an electron-withdrawing leaving group, if appropriate in the presence of a diluent and if appropriate in the presence of an acid-binding agent, and, if appropriate, an acid is then added on or the reaction is followed by a physical separation method.

Finally, it has been found that the new aminomethyl heterocyclic compounds of the general formula (I) have an action against pests, in particular against fungal pests.

Surprisingly, the aminomethyl heterocyclic compounds of the general formula (I) according to the invention have a better fungicidal activity than the aminomethyldioxolanes known from the prior art, such as, for example 2-isobutyl-2-methyl-4-(1-piperidinylmethyl)-1,3-dioxolane or 2-methyl-2-nonyl-4-di-n-butylaminomethyl-1,3-dioxolane, which are closely related compounds chemically and from the point of view of their action.

Formula (I) provides a general definition of the aminomethyl heterocyclic compounds according to the invention. Preferred compounds of the formula (I) are those in which X represents oxygen or sulphur, R represents hydrogen, or represents straight-chain or branched alkyl with 1 to 6 carbon atoms, or represents phenyl or cyclohexyl, in each case optionally mono-, di- or trisubstituted by identical or different substituents from the group comprising alkyl with 1 to 4 carbon atoms and/or halogen, and $R^1$ and $R^2$ independently of one another each represent hydrogen; or represent in each case straight-chain or branched alkyl with 1 to 12 carbon atoms, alkenyl with 3 to 8 carbon atoms, alkinyl with 3 to 8 carbon atoms, hydroxyalkyl with 2 to 6 carbon atoms, alkoxyalkyl or dialkoxyalkyl with in each case 1 to 6 carbon atoms or hydroxyalkoxyalkyl with 2 to 6 carbon atoms in the individual alkyl parts, alkoxycarbonylalkyl with 1 to 6 carbon atoms in the alkoxy and alkyl part, or represent in each case straight-chain or branched dioxolanylalkyl, dioxanylalkyl or oxolanylalkyl with in each case 1 to 4 carbon atoms in the alkyl part, or represent cycloalkyl or cycloalkylalkyl with in each case 3 to 7 carbon atoms in the cycloalkyl part and where appropriate 1 to 4 carbon atoms in the straight-chain or branched alkyl part and in each case optionally mono- or polysubstituted in the cycloalkyl part by identical or different substituents, possible substituents in each case being: halogen and in each case straight-chain or branched alkyl, alkoxy, halogenoalkyl and halogenoalkoxy with in each case 1 to 4 carbon atoms and where appropriate 1 to 9 identical or different halogen atoms; or furthermore represent arylalkyl, arylalkenyl or aryl with in each case 6 to 10 carbon atoms in the aryl part and where appropriate up to 6 carbon atoms in the straight-chain or branched alkyl or alkenyl part, in each case optionally mono- or polysubstituted in the aryl part by identical or different substituents, possible substituents on the aryl in each case being: halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and where appropriate 1 to 9 identical or different halogen atoms, or $R^1$ and $R^2$, together with the nitrogen atom to which they are bonded, represent a saturated 5- to 7-membered heterocyclic radical which can optionally contain a further hetero atom, in particular nitrogen, oxygen or sulphur, and is optionally mono- or polysubstituted by identical or different substituents, possible substituents being: in each case straight-chain or branched alkyl and hydroxyalkyl with in each case 1 to 4 carbon atoms.

Particularly preferred compounds of the formula (I) are those in which

X represents oxygen or sulphur,

R represents hydrogen, methyl, ethyl, neopentyl, cyclohexyl or phenyl and $R^1$ and $R^2$ independently of one another in each case represent hydrogen, methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, diethoxyethyl, methoxycarbonylmethyl, methoxycarbonylethyl, methoxycarbonylpropyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, dioxanylethyl, oxolanylmethyl or oxolanylethyl, cyclopropylmethyl, cyclopropylethyl, cyclopropylpropyl, cyclopentyl, cyclopentylmethyl, cyclohexyl or cyclohexylmethyl, in each case optionally mono-, di-, tri-, tetra- or pentasubstituted by identical or different substituents from the group comprising fluorine, chlorine, bromine, methyl, ethyl, n- or i-propyl and/or n-, i-, s- or t-butyl, or represent phenyl, benzyl or phenethyl, in each case optionally mono-, di- or tri-substituted by identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluoromethyl, trifluoromethoxy, trifluoromethylthio, methoxycarbonyl, ethoxycarbonyl and methoximinomethyl, or $R^1$ and $R^2$, together with the nitrogen atom to which they are bonded, represent a heterocyclic radical of the formula

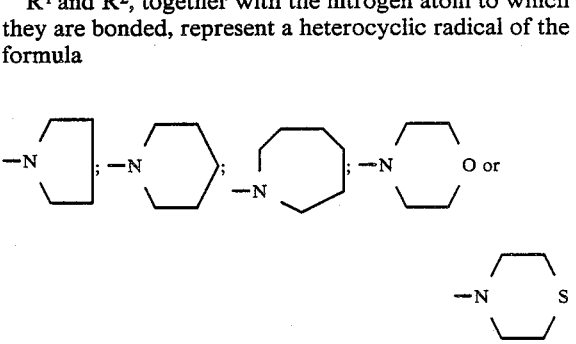

which is optionally mono-, di- or trisubstituted by identical or different substituents, possible substituents being: methyl, ethyl, and hydroxymethyl.

Especially preferred compounds of the formula (I) are those in which

X represents oxygen or sulphur,

R represents hydrogen, methyl or ethyl and

R¹ and R² independently of one another, each represent hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, oxolanylmethyl, oxolanylethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl, or R¹ and R², together with the nitrogen atom to which they are bonded, represent a heterocyclic radical of the formula

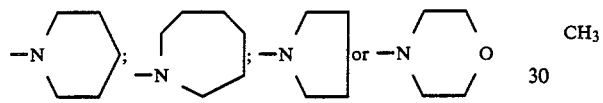

which is optionally mono-, di- or trisubstituted by identical or different substituents, possible substituents being: methyl, ethyl and hydroxymethyl.

Halogen, including halogen in combinations, denotes fluorine, chlorine, bromine or iodine, in particular fluorine, chlorine or bromine, unless defined otherwise.

Addition products of acids and those aminomethyl heterocyclic compounds of the formula (I) in which the substituents X, R, R¹ and R² have the meanings which have already been mentioned as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono-, di- and trifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid, and furthermore saccharine.

The following aminomethyl heterocyclic compounds of the general formula (I) may be mentioned specifically, in addition to the compounds mentioned in the preparation examples:

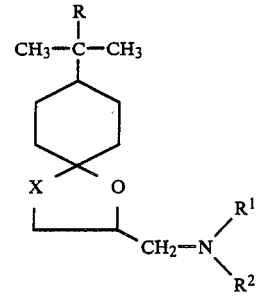

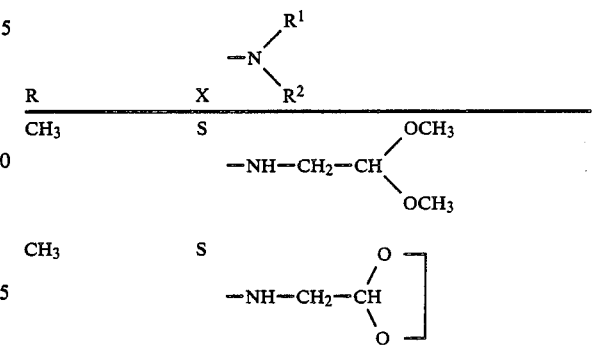

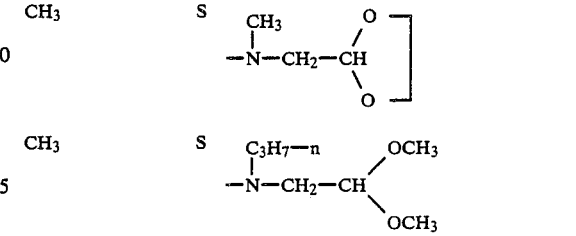

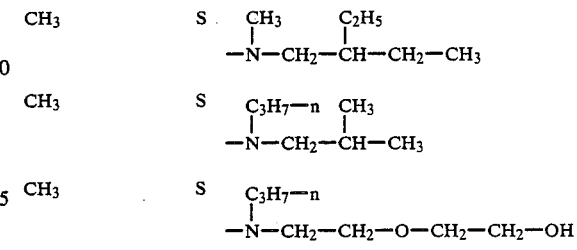

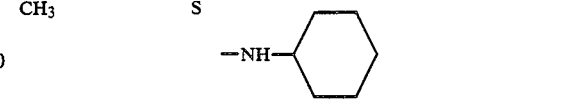

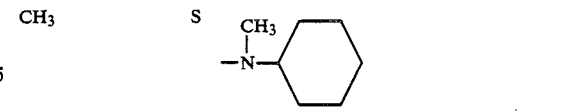

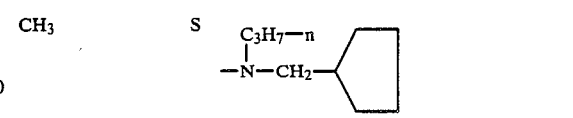

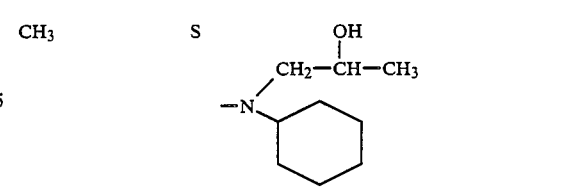

-continued
(I)
| R | X | -N(R¹)(R²) |
|---|---|---|
| CH₃ | S | 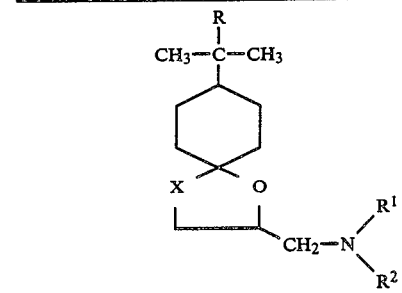 |
| CH₃ | S | 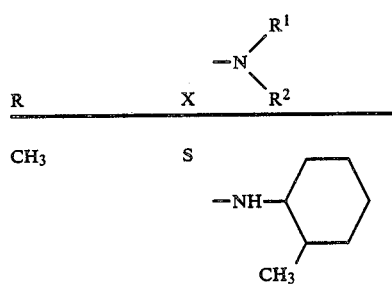 |
| C₂H₅ | S | 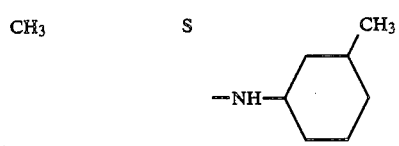 |
| C₂H₅ | S | 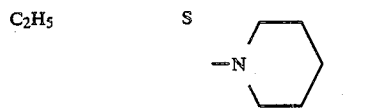 |
| C₂H₅ | S | 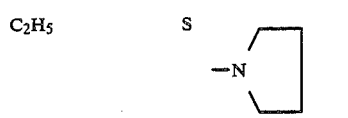 |
| C₂H₅ | S |  |
| C₂H₅ | S | 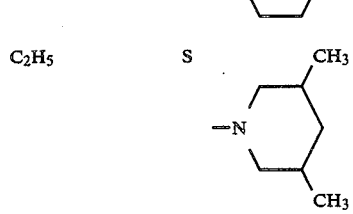 |
| C₂H₅ | S | 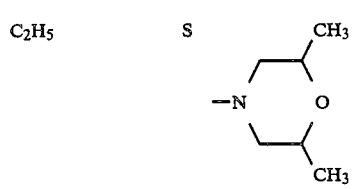 |
-continued
(I)
| R | X | -N(R¹)(R²) |
|---|---|---|
| C₂H₅ | S | 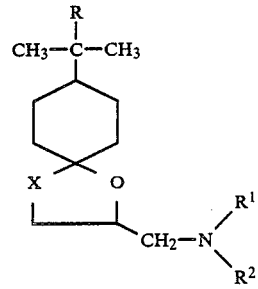 |
| C₂H₅ | S | 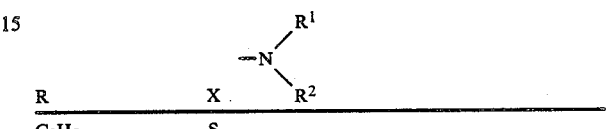 |
| C₂H₅ | S | —NH—CH₂—C≡CH |
| C₂H₅ | S | —NH—CH₂—CH₂—C≡CH |
| C₂H₅ | S | 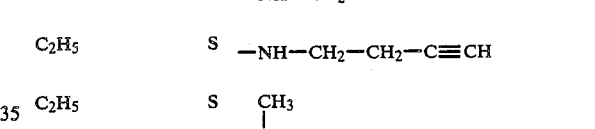 |
| CH₃ | O | 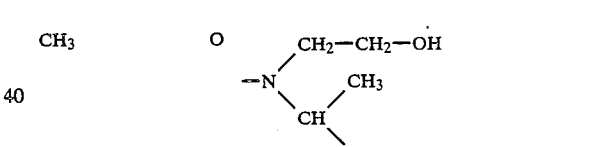 |
| CH₃ | O | 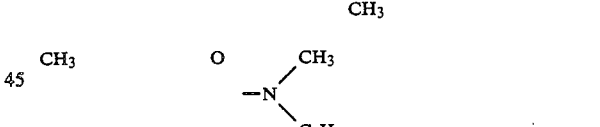 |
| CH₃ | O | 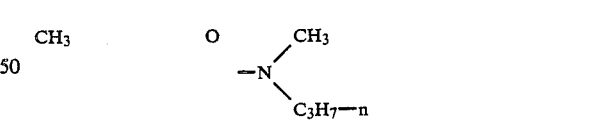 |
| CH₃ | O | 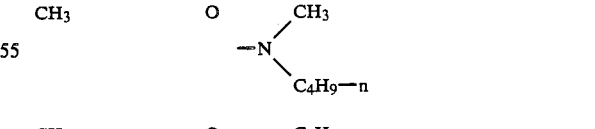 |
| CH₃ | O | 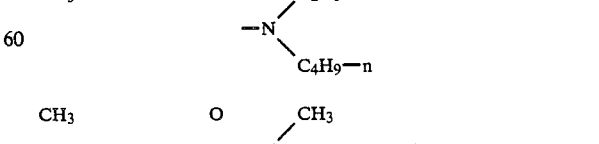 |
| CH₃ | O | 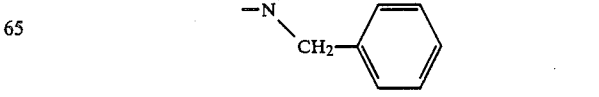 |

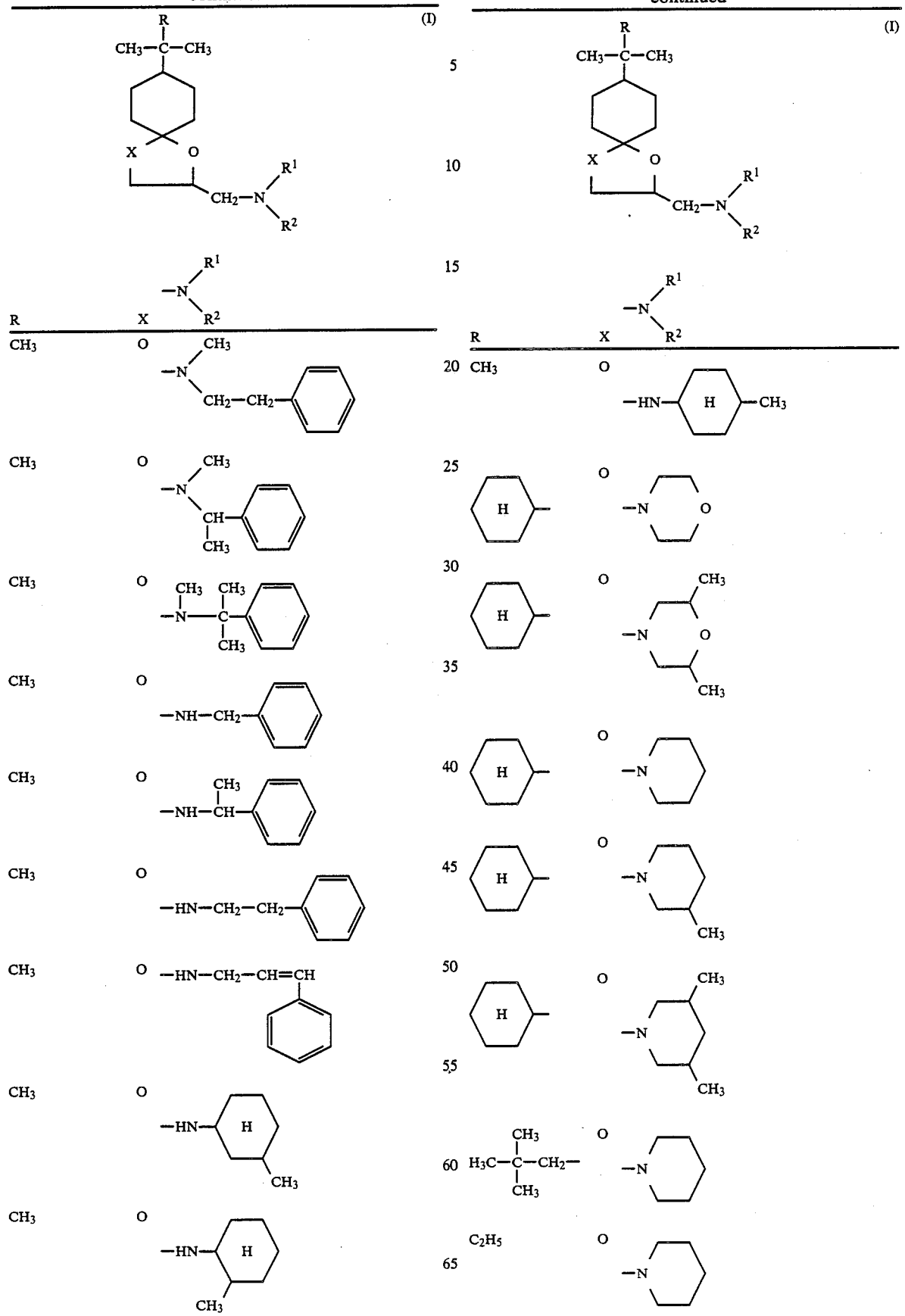

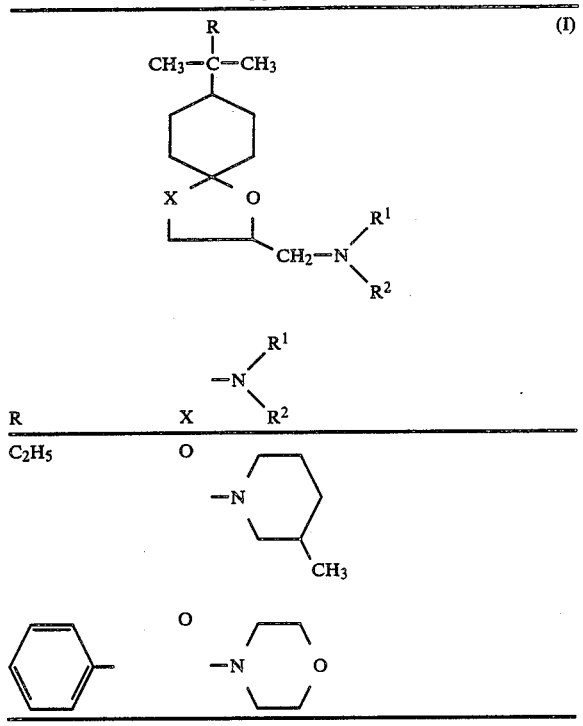

| R | X | –N⟨R¹/R² |
|---|---|---|
| C₂H₅ | O | –N(piperidine with CH₃) |
| phenyl | O | –N(morpholine) |

If, for example, 8-t-butyl-2-chloromethyl-1,4-dioxaspiro[4,5]decane and piperidine are used as starting substances, the course of the reaction in process (a) according to the invention can be represented by the following equation:

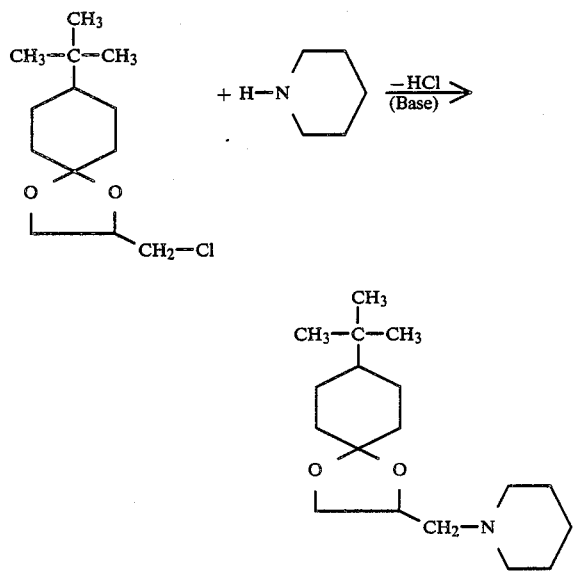

If, for example, 8-t-butyl-2-methylaminomethyl-1,4-dioxaspiro[4,5]decane and allyl bromide are used as starting substances, the course of the reaction in process (b) according to the invention can be represented by the following equation:

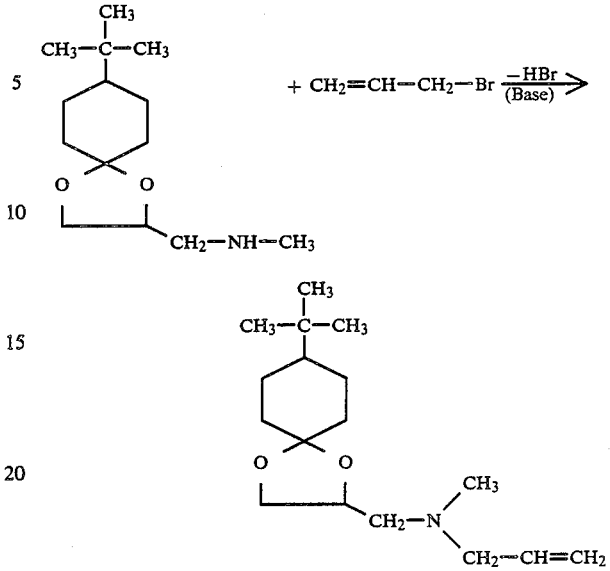

Formula (II) provides a general definition of the substituted heterocyclic compounds required as starting substances for carrying out process (a) according to the invention. In this formula (II), R and X preferably represent those radicals which have already been mentioned for these substituents in connection with the description of the substances of the formula (I) according to the invention.

$E^1$ preferably represents halogen, in particular iodine, chlorine or bromine, or represents alkylsulphonyloxy, optionally substituted by halogen, such as fluorine, chlorine, bromine or iodine, or represents arylsulphonyloxy, optionally substituted, inter alia, by alkyl with 1 to 4 carbon atoms, such as, for example, methanesulphonyloxy, trifluoromethanesulphonyloxy or p-toluenesulphonyloxy.

The substituted heterocyclic compounds of the formula (II) are known (compare, for example, J. org. Chem. 38, 834–835 [1973]), or they can be prepared by processes analogous to known processes (compare, for example, Tetrahedron Lett. 23, 47–50, [1982]; Liebigs Ann. Chem. 1984, 1298–1301; Z. Naturforsch. B, Anorg. Chem., Org. Chem. 4013, 393–397 [1985] or J. org. Chem. 51, 1894–1897 [1986] and the preparation examples), for example by a procedure in which generally known cyclic ketones of the formula (V)

(V)

in which
R has the abovementioned meaning, are cyclized with generally known alcohols of the formula (VI)

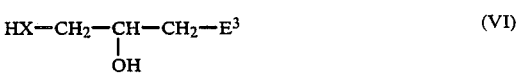

(VI)

in which
X has the abovementioned meaning and $E^3$ represents halogen or hydroxyl, if appropriate in the presence of a diluent, such as, for example, toluene, and if appropriate in the presence of an acid catalyst, such as, for example, p-toluenesulphonic acid, at temperatures between 40° C. and 150° C., and if appropriate, in cases where $E^3$ in formula (VI) represents a hydroxyl group, in a 2nd stage the hydroxymethyl heterocyclic compounds thus obtainable, of the formula (VII)

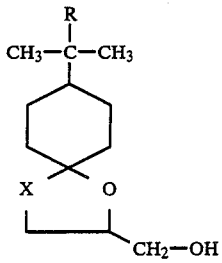

(VII)

in which

X and R have the abovementioned meaning, are reacted with optionally substituted alkyl- or arylsulphonyl halides of the formula (VIII)

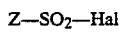

(VIII)

in which

Hal represents halogen, in particular chlorine, and

Z represents alkyl, optionally substituted by halogen, such as fluorine, chlorine, bromine or iodine, or represents aryl which is optionally substituted by alkyl with 1 to 4 carbon atoms, such as, in particular, methyl, trifluromethyl or 4-methylphenyl, if appropriate in the presence of a diluent, such as, for example, diethyl ether, and if appropriate in the presence of an acid-binding agent, such as, for example, pyridine or triethylamine, at temperatures between −20° C. and +100° C.

The geometric isomers thereby obtainable can be either further reacted as mixtures in process (a) according to the invention or separated by customary separation methods (chromatography or crystallization).

Formula (III) provides a general definition of the amines furthermore required as starting substances for carrying out process (a) according to the invention. In this formula (III), $R^1$ and $R^2$ preferably represent those radicals which have already been mentioned for these substituents in connection with the description of the substances of the formula (I) according to the invention.

The amines of the formula (III) are generally known compounds of organic chemistry.

Formula (Ia) provides a general definition of the aminomethyl heterocyclic compounds required as starting substances for carrying out process (b) according to the invention. In this formula (Ia), X, R and $R^1$ preferably represent those radicals which have already been mentioned for these substituents in connection with the description of the substances of the formula (I) according to the invention.

The aminomethyl heterocyclic compounds of the formula (Ia) are compounds according to the invention and are obtainable with the aid of process (a) according to the invention.

Formula (IV) provides a general definition of the alkylating agents furthermore required as starting substances for carrying out process (b) according to the invention. In this formula (IV), $R^{2-1}$ preferably represents in each case straight-chain or branched alkyl with 1 to 12 carbon atoms, alkenyl with 3 to 8 carbon atoms, alkinyl with 3 to 8 carbon atoms, hydroxyalkyl with 2 to 6 carbon atoms, alkoxyalkyl or dialkoxyalkyl with 1 to 6 carbon atoms or hydroxyalkoxyalkyl with 2 to 6 carbon atoms in the individual alkyl parts, or represents in each case straight-chain or branched dioxolanylalkyl or dioxanylalkyl with in each case 1 to 4 carbon atoms in the alkyl part, or represents cycloalkyl or cycloalkylalkyl with in each case 3 to 7 carbon atoms in the cycloalkyl part and where appropriate 1 to 4 carbon atoms in the straight-chain or branched alkyl part, in each case optionally mono- or polysubstituted in the cycloalkyl part by identical or different substituents, possible substituents in each case being: halogen and in each case straight-chain or branched alkyl, alkoxy, halogenoalkyl or halogenoalkoxy with in each case 1 to 4 carbon atoms and where appropriate 1 to 9 identical or different halogen atoms; or furthermore represents arylalkyl or arylalkenyl with in each case 6 to 10 carbon atoms in the aryl part and up to 6 carbon atoms in the straight-chain or branched alkyl or alkenyl part, in each case optionally mono- or polysubstituted in the aryl part by identical or different substituents, possible substituents on the aryl in each case being: halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and where appropriate 1 to 9 identical or different halogen atoms.

$R^{2-1}$ particularly preferably represents methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, dimethoxyethyl, dimethoxypropyl, di-ethoxyethyl, methoxycarbonylmethyl, methoxycarbonylethyl, methoxycarbonylpropyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, dioxoanylethyl, oxolanylmethyl or oxolanylethyl, or represents cyclopropyl, cyclopropylmethyl, cyclopropylethyl, cyclopropylpropyl, cyclopentyl, cyclopentylmethyl, cyclohexyl or cyclohexylmethyl, in each case optionally mono-, di-, tri-, tetra- or pentasubstituted by identical or different substituents from the group comprising fluorine, chlorine, bromine, methyl, ethyl, n- or i-propyl and/or n-, i-, s- or t-butyl, or represents benzyl or phenethyl, in each case optionally mono-, di- or trisubstituted by identical or different substituents, possible substituents in each case being: fluorine, chlorine, bromine, cyano, nitro, methyl, ethyl, n- or i-propyl, n-, i-, s- or t-butyl, methoxy, ethoxy, methylthio, trifluormethyl, trifluoromethoxy, trifluoromethylthio, methoxycarbonyl, ethoxycarbonyl and methoximinomethyl.

$R^{2-1}$ especially preferably represents methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylethyl, ethoxycarbonylpropyl, propoxycarbonylmethyl, propoxycabonylethyl, propoxycarbonylpropyl, dioxolanylmethyl, dioxolanylethyl, dioxanylmethyl, oxolanylmethyl, oxolanylethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl $E^2$ preferably represents halogen, in particular chlorine, bromine or iodine, or represents alkylsulphonyloxy or alkoxysulphonyloxy with in each case 1 to 4 carbon atoms and in each case optionally substituted by halogen, such as fluorine, chlorine, bromine or iodine, or represents arylsulphonyloxy which is optionally substituted by, for example, alkyl with 1 to 4 carbon atoms, such as, for example, methanesulphonyloxy, methoxysulphonyloxy or p-toluenesulphonyloxy.

The alkylating agents of the formula (IV) are likewise generally known compounds of organic chemistry or are obtainable by processes analogous to generally known processes.

Possible diluents for carrying out processes (a) and (b) according to the invention are inert organic solvents or aqueous systems. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether; ketones, such as acetone or butanone; nitriles, such as acetonitrile or propionitrile; amides, such as dimethylformamide, dimethylacetamide, N-methylformanilide, N-methylpyrrolidone or hexamethylphosphoric acid triamide; esters, such as ethyl acetate; sulphoxides, such as dimethylsulphoxide, or alcohols, such as methanol, ethanol or propanol.

If appropriate, processes (a) and (b) according to the invention can also be carried out in a two-phase system, such as, for example, water/toluene or water/methylene chloride, if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dibenzyldimethyl-ammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride or trimethylbenzylammonium chloride. It is also possible for processes (a) and (b) according to the invention to be carried out without the addition of a solvent.

Possible acid-binding agents for carrying out processes (a) and (b) according to the invention are all the inorganic and organic bases which can usually be employed. Bases which are preferably used are alkali metal hydroxides, alcoholates, carbonates or bicarbonates, such as, for example, sodium hydroxide, sodium methylate, sodium ethylate, sodium carbonate or sodium bicarbonate, or tertiary amines, such as, for example, triethylamine, N,N-dimethylaniline, pyridine, 4-(N,N-dimethylamino)pyridine, diazabicyclooctane (DABCO), diazabicyclononene (DBN) or diazabicycloundecene (DBU).

It is also possible for the amines of the formulae (III) or (Ia) used as participants in the reaction to be used simultaneously in a corresponding excess as the acid-binding agent.

The reaction temperatures can be varied within a substantial range in carrying out processes (a) and (b) according to the invention. THe reaction is in general carried out at temperatures between +20° C. and +200° C., preferably at temperatures between 80° C. and +180° C.

Processes (a) and (b) according to the invention are in general carried out under normal pressure. However, it is also possible for the processes to be carried out under increased pressure in the range between 1 and 10 atmospheres. The procedure under increased pressure is advisable, in particular, if one or more participants in the reaction are gaseous under normal pressure and at the required reaction temperature.

For carrying out process (a) according to the invention, in general 1.0 to 10.0 mols, preferably 1.0 to 5.0 mmols, of amine of the formula (III) and if appropriate 1.0 to 10.0 mols, preferably 1.0 to 5.0 mols, of acid-binding agent and if appropriate 0.1 to 1.0 mol of phase transfer catalyst are employed per mol of substituted heterocyclic compound of the formula (II).

For carrying out process (b) according to the invention, in general 1.0 to 5.0 mols, preferably 1.0 to 2.0 mols, of alkylating agent of the formula (IV) and 1.0 to 5.0 mols, preferably 1.0 to 2.0 mols, of acid-binding agent and if appropriate 0.1 to 1.0 mol of phase transfer catalyst are employed per mol of aminomethyl heterocyclic compound of the formula (Ia).

In both cases, the reaction is carried out and the reaction products of the formula (I) are worked up and isolated by customary methods.

The following acids can preferably be used to prepare acid addition salts of the compounds of the formula (I): hydrogen halide acids, such as, for example, hydrochloric acid and hydrobromic acid, in particular hydrochloric acid, and furthermore phosphoric acid, nitric acid, sulphuric acid, mono-, di- and trifunctional carboxylic acids and hydroxycarboxylic acids, such as, for example, acetic acid, maleic acid, succinic acid, furmaric acid, tartaric acid, citric acid, salicylic acid, sorbic acid and lactic acid, and sulphonic acids, such as, for example, p-toluenesulphonic acid and 1,5-naphthalenedisulphonic acid, and in addition saccharine.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and they can be isolated in a known manner, for example by filtration, and if appropriate purified by washing with an inert organic solvent.

The active compounds according to the invention exhibit a powerful action against pests and can be used in practice for combating undesirable harmful organisms. The active compounds are suitable for use, inter alia, as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, Pythium ultimum; Phytophthora species, such as, for example, Phytophthora infestans; Pseudoperonospora species, such as, for example, Pseudoperonospora humuli or Pseudoperonospora cubensis; Plasmopara species, such as, for example, Plasmopara viticola; Peronospora species, such as, for example, Peronospora pisi or P. brassicae; Erysiphe species, such as, for example, Erysiphe graminis; Sphaerotheca species, such as, for example, Sphaerotheca fuliginea; Podosphaera species, such as, for example, Podosphaera leucotricha; Venturia species, such as, for example, Venturia inaequalis; Pyrenophora species, such as, for example, Pyrenophora teres or P. graminea (conidia form: Drechslera, syn: Helminthosporium); Cochliobolus species, such as, for example, Cochliobolus sativus (conidia form: Drechslera, syn: Helminthosporium); Uromyces species, such as, for example, Uromyces appendiculatus; Puccinia species, such as, for example, Puccinia recondita; Tilletia species, such as, for example, Tilletia caries; Ustilago species, such as, for example, Ustilago nuda or Ustilago avenae; Pellicularia species, such as, for example, Pellicularia sasakii; Pyricularia species, such as, for example, Pyricularia oryzae; Fusarium species, such as, for example, Fusarium culmorum; Botrytis species, such as, for example, Botrytis cinerea; Septoria species, such as, for example, Septoria nodorum; Leptosphaeria species, such as, for example, Leptosphaeria nodorum; Cercospora species, such as, for example, Cercospora canescens; Alternaria species, such as, for example, Alternaria brassicae and Pseudocercosporella species, such as, for example, Pseudocercosporella herpotrichoides.

The good toleration, by plants, of the active compounds, at the concentrations required for combating plant diseases, permits treatment of above-ground parts of plants, of vegetative propagation stock and seeds, and of the soil.

The active compounds according to the invention can thereby be used with particularly good success for combating cereal diseases, such as, for example, against the leaf spot disease of barley causative organism (Pyrenophora teres) or against the leaf spot disease of wheat causative organism (Cochliobolus sativus), as well as against mildew and rust species, or for combating diseases in fruit and vegetable growing, such as, for example, against the apple scab causative organism (Venturia inaequalis). The active compounds according to the invention moreover show a good in vitro activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suiable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesions such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom by further dilution, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

In the treatment of soil, active compound concentrations of 0.00001 to 0.1% by weight, preferably 0.0001 to 0.02% by weight, are required at the place of action.

PREPARATION EXAMPLES

EXAMPLE 1

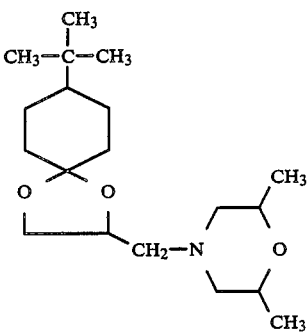

(Process a)

12.3 g (0.05 mol) of 8-t-butyl-2-chloromethyl-1,4-dioxaspiro[4,5]decane (cis-trans mixture) and 23 g (0.2 mol) of cis-2,6-dimethylmorpholine are stirred together at 130° C. for 15 hours. For working up, 100 ml of ethyl acetate are added to the cooled reaction mixture and the mixture is washed five times with 50 ml of water each time and dried over sodium sulphate and the solvent is removed in vacuo.

15.8 g (97% of theory) of 8-t-butyl-2-(2,6-dimethylmorpholin-4-yl-methyl)-1,4-dioxaspiro[4,5]decane are obtained as an oil of refractive index $n_D^{20}$: 1.4756, which, according to analysis by gas chromatography, is predominantly present as a cis/cis and cis/trans diastereomer mixture.

PREPARATION OF THE STARTING COMPOUNDS

EXAMPLE II-1:

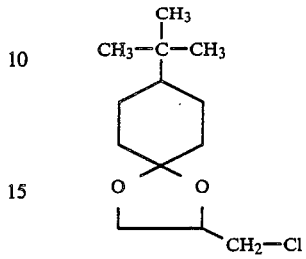

100 g (0.648 mol) of 4-t-butylcyclohexanone, 143.2 g (1.296 mols) of 3-chloro-1,2-propanediol and 12.3 g (0.0648 mol) of p-toluenesulphonic acid are heated under reflux in 1 l of toluene over a water separator for 15 hours. The cooled reaction mixture is washed five times with 300 ml of saturated aqueous sodium bicarbonate solution each time, dried over sodium sulphate and freed from the solvent in vacuo.

159.5 g (99% of theory) of 8-t-butyl-2-chloromethyl-1,4-dioxaspiro[4,5]decane of refractive index $n_D^{20}$: 1.4774, which, according to analysis by gas chromatography and the proton nuclear magnetic resonance spectrum, is in the form of a cis-trans (55:45) mixture.

The following aminomethyl heterocyclic compounds of the general formula (I) are obtained in a corresponding manner and in accordance with the general statements on the preparation:

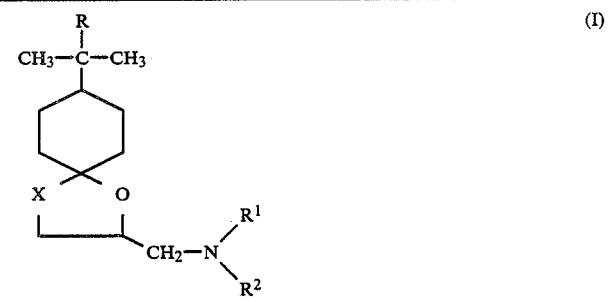

| Example No. | X | R | $-N\begin{smallmatrix}R^1\\R^2\end{smallmatrix}$ | Physical Properties |
|---|---|---|---|---|
| 2 | O | CH₃ | —N(piperidine) | $n_D^{20}$: 1.4830 |
| 3 | O | CH₃ | —N(morpholine) | $n_D^{20}$: 1.4833 |

-continued

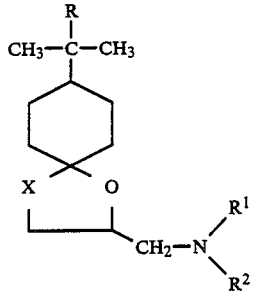
(I)

| Example No. | X | R | $-N\begin{smallmatrix}R^1\\R^2\end{smallmatrix}$ | Physical Properties |
|---|---|---|---|---|
| 4 | O | CH₃ | 3-methylpiperidin-1-yl | $n_D^{20}$: 1.4801 |
| 5 | O | CH₃ | 3,5-dimethylpiperidin-1-yl | $n_D^{20}$: 1.4767 |
| 6 | O | CH₃ | hexahydroazepin-1-yl | $n_D^{20}$: 1.4867 |
| 7 | O | CH₃ | —NH—cyclopentyl | $n_D^{20}$: 1.4856 |
| 8 | O | CH₃ | —NH—cyclohexyl | $n_D^{20}$: 1.4861 |
| 9 | S | CH₃ | —NH—CH₂—CH(CH₃)₂ | $n_D^{20}$: 1.4916 |
| 10 | S | CH₃ | —NH—CH₂—CH(CH₃)₂ | $n_D^{20}$: 1.5298 |
| 11 | S | CH₃ | 2,6-dimethylmorpholin-4-yl | $n_D^{20}$: 1.5012 |
| 12 | S | CH₃ | 3,5-dimethylpiperidin-1-yl | Melting Point 43° C. |
| 13 | S | CH₃ | piperidin-1-yl | Melting Point 48° C. |

-continued

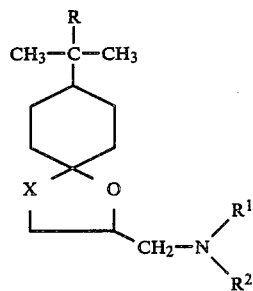
(I)

| Example No. | X | R | $-N\begin{smallmatrix}R^1\\R^2\end{smallmatrix}$ | Physical Properties |
|---|---|---|---|---|
| 14 | S | CH₃ | —NH—(CH₂)₃—OC₂H₅ | $n_D^{20}$: 1.4959 |
| 15 | O | CH₃ | —NH—(2-methylcyclohexyl, H) | $n_D^{20}$: 1.4872 |
| 16 | O | CH₃ | —NH—(3-methylcyclohexyl, H) | $n_D^{20}$: 1.4872 |
| 17 | O | CH₃ | —NH—(4-methylcyclohexyl, H) | $n_D^{20}$: 1.4808 |
| 18 | O | C₂H₅ | —N(piperidinyl) | $n_D^{20}$: 1.4851 |
| 19 | O | C₂H₅ | —N(3-methylpiperidinyl) | $n_D^{20}$: 1.4814 |
| 20 | O | C₂H₅ | —N(azocanyl) | $n_D^{20}$: 1.4886 |
| 21 | O | C₂H₅ | 3,5-dimethylcyclohexyl | $n_D^{20}$: 1.4793 |
| 22 | O | C₂H₅ | —N(morpholinyl) | $n_D^{20}$: 1.4847 |

-continued

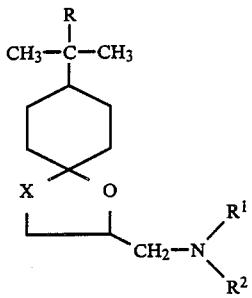

| Example No. | X | R | $-N\begin{smallmatrix}R^1\\R^2\end{smallmatrix}$ | Physical Properties |
|---|---|---|---|---|
| 23 | O | C₂H₅ | -N(CH₂CH(CH₃)OCH(CH₃)CH₂) (2,6-dimethylmorpholino) | $n_D^{20}$: 1.4785 |
| 24 | O | CH₃ | —NH—CH₂—C₆H₅ | $n_D^{20}$: 1.5088 |
| 25 | O | CH₃ | —NH—CH(CH₃)—C₆H₅ | $n_D^{20}$: 1.5088 |
| 26 | O | CH₃ | piperidino | $n_D^{20}$: 1.4858 |
| 27 | O | CH₃ | 3-methylpiperidino | $n_D^{20}$: 1.4874 |
| 28 | O | CH₃ | 2,6-dimethylmorpholino | $n_D^{20}$: 1.4829 |
| 29 | O | cyclohexyl (H) | piperidino | Melting point: 37–48°C. |
| 30 | O | cyclohexyl (H) | 3-methylpiperidino | $n_D^{20}$: 1.4993 |

-continued

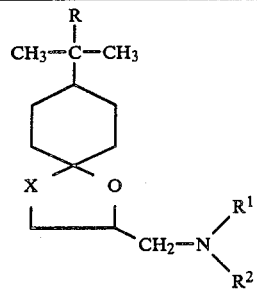

| Example No. | X | R | -N(R¹)(R²) | Physical Properties |
|---|---|---|---|---|
| 31 | O | cyclohexyl-H | -N(CH(CH₃))₂ morpholine (2,6-dimethyl) | $n_D^{20}$: 1.4958 |
| 32 | O | CH₃ | -N(C₂H₅)₂ | $n_D^{20}$: 1.4660 |
| 33 | O | CH₃ | -NH-(CH₂)₃-OC₂H₅ | $n_D^{20}$: 1.470 |
| 34 | O | CH₃ | -NH-CH₂-CH(C₂H₅)₂ | $n_D^{20}$: 1.4672 |
| 35 | O | CH₃ | -N(CH₂-CH₂-OH)(CH(CH₃)₂) | $n_D^{20}$: 1.4757 |
| 36 | O | CH₃ | -N(CH₃)(C₂H₅) | $n_D^{20}$: 1.4662 |
| 37 | O | CH₃ | -N(CH₃)((CH₂)₃-CH₃) | $n_D^{20}$: 1.4653 |
| 38 | O | CH₃ | -N(CH₃)((CH₂)₂-CH₃) | $n_D^{20}$: 1.4663 |
| 39 | O | CH₃ | -N(C₂H₅)((CH₂)₃-CH₃) | $n_D^{20}$: 1.4649 |
| 40 | O | CH₃ | -N(CH₃)-CH₂-C₆H₅ | $n_D^{20}$: 1.5079 |
| 41 | O | cyclohexyl-H | -N(C₂H₅)₂ | $n_D^{20}$: 1.4893 |
| 42 | O | CH₃ | -NH-(CH₂)₂-OCH₃ | $n_D^{20}$: 1.4692 |

-continued

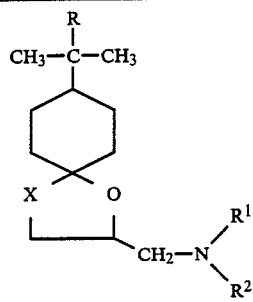
(I)

| Example No. | X | R | $-N\begin{smallmatrix}R^1\\R^2\end{smallmatrix}$ | Physical Properties |
|---|---|---|---|---|
| 43 | O | CH₃ | —NH—CH₃ | Boiling point 116–120° C./0.9 mm |
| 44 | O | CH₃ | —N(C₂H₅)((CH₂)₂—CH₃) | $n_D^{20}$: 1.4662 |
| 45 | O | (CH₃)₃C—CH₂— | —N(C₂H₅)₂ | $n_D^{20}$: 1.4733 |
| 46 | O | C₂H₅ | —N(C₂H₅)₂ | $n_D^{20}$: 1.4651 |
| 47 | O | CH₃ | —NH—CH(CH₃)—C₆H₅ | $n_D^{20}$: 1.5050 |
| 48 | O | CH₃ | —N(CH₃)—CH₂—CH=CH—C₆H₅ | $n_D^{20}$: 1.5254 |
| 49 | O | CH₃ | —NH—CH₂—CH₂—C₆H₅ | $n_D^{20}$: 1.5123 |
| 50 | O | CH₃ | —N(CH₃)-(4-methylcyclohexyl) | |
| 51 | O | CH₃ | —NH—CH(CH₃)-cyclohexyl | $n_D^{20}$: 1.4836 |
| 52 | O | C₂H₅ | —NH-cyclohexyl | $n_D^{20}$: 1.4871 |

-continued

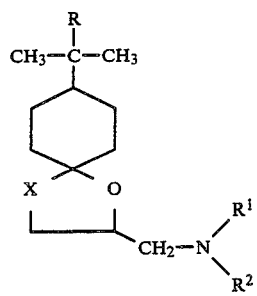
(I)

| Example No. | X | R | $-N\begin{smallmatrix}R^1\\R^2\end{smallmatrix}$ | Physical Properties |
|---|---|---|---|---|
| 53 | O | C₂H₅ | -NH-（3-methylcyclohexyl） | $n_D^{20}$: 1.4838 |
| 54 | O | CH₃ | -N(CH₂-CH(OH)-CH₃)₂ | $n_D^{20}$: 1.4788 |
| 55 | O | C₂H₅ | -NH-(CH₂)₂-OCH₃ | $n_D^{20}$: 1.4720 |
| 56 | O | C₂H₅ | -NH-(CH₂)₃-CH₃ | $n_D^{20}$: 1.4708 |
| 57 | O | CH₃ | -N(CH₃)-(CH₂)₂-C₆H₅ | Boiling point 157° C. |
| 58 | O | CH₃ | -N(CH₃)-CH(CH₃)-C₆H₅ | |
| 59 | O | CH₃ | -N(CH₃)-CH(CH₃)-C₆H₅ | |
| 60 | O | CH₃ | -N(CH₂-CH(C₂H₅)₂)(CH₂-COOCH₃) | $n_D^{20}$: 1.4706 |
| 61 | O | CH₃ | -N((CH₂)₃-OC₂H₅)((CH₂)₂-CH₃) | $n_D^{20}$: 1.4647 |
| 62 | O | CH₃ | -N(piperidinyl) | |

X  CH₃—(CH₂)₁₁—C₆H₄—SO₃H

-continued
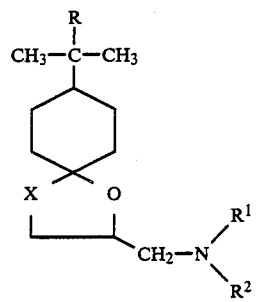
(I)
| Example No. | X | R | $-N\begin{matrix}R^1\\R^2\end{matrix}$ | Physical Properties |
|---|---|---|---|---|
| 63 | O | CH₃ | ![3,5-dimethylpiperidinyl] | |
| | | | × CH₃—(CH₂)₁₁—C₆H₄—SO₃H | |
| 64 | O | CH₃ | ![azepanyl] | |
| | | | × CH₃—(CH₂)₁₁—C₆H₄—SO₃H | |
| 65 | O | CH₃ | —NH—(2-methylcyclohexyl) | |
| | | | × CH₃—(CH₂)₁₁—C₆H₄—SO₃H | |
| 66 | O | CH₃ | —NH—(4-methylcyclohexyl, H) | |
| | | | × CH₃—(CH₂)₁₁—C₆H₄—SO₃H | |
| 67 | O | CH₃ | —NH—(3-methylcyclohexyl, H) | |

-continued $$\text{(I)}$$

| Example No. | X | R | $-N\begin{matrix}R^1\\R^2\end{matrix}$ | Physical Properties |
|---|---|---|---|---|
|  |  |  | —CH₃—(CH₂)₁₁—⟨C₆H₄⟩—SO₃H |  |
| 68 | O | CH₃ | —N⟨3-methylpiperidine⟩ |  |
|  |  |  | x CH₃—(CH₂)₁₁—⟨C₆H₄⟩—SO₃H |  |
| 69 | O | CH₃ | —N((CH₂)₃—CH₃)((CH₂)₃—CH₃) | Boiling point 136° C. |
| 70 | O | C₂H₅ | —N((CH₂)₃—CH₃)(CH₂—COOCH₃) | $n_D^{20}$: 1.4713 |
| 71 | O | CH₃ | —N(CH₂—CH₂—OCH₃)((CH₂)₂—CH₃) | $n_D^{20}$: 1.4651 |
| 72 | O | C₂H₅ | —N(CH₂—CH₂—OCH₃)(C₂H₅) | $n_D^{20}$: 1.4685 |
| 73 | O | C₂H₅ | —N(CH₂—CH₂—OCH₃)((CH₂)₂—CH₃) | $n_D^{20}$: 1.4687 |
| 74 | O | CH₃ | —N(CH₂—CH₂—OCH₃)(C₂H₅) | $n_D^{20}$: 1.4659 |
| 75 | S | CH₃ | —N⟨3-methylpiperidine⟩ | $\eta_D^{20}$ 1.4988 |

-continued
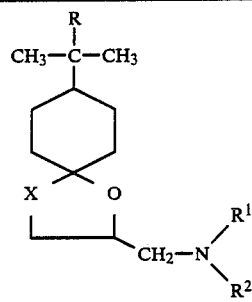
(I)
| Example No. | X | R | $-N\begin{array}{c}R^1\\R^2\end{array}$ | Physical Properties |
|---|---|---|---|---|
| 76 | S | CH₃ | —N(morpholine)O | Melting point 37–57° C. |
| 77 | S | CH₃ | —NH—CH₂—CH(C₂H₅)(C₂H₅) | $n_D^{20}$: 1.4016 |
| 78 | S | CH₃ | —NH—cyclohexyl (H) | ¹H-NMR* 4.2 – 4.4 3.0 – 3.1 2.7 – 2.9 |
| 79 | S | CH₃ | —NH—CH₂—cyclohexyl (H) | $n_D^{20}$: 1.5058 |
| 80 | S | CH₃ | —NH—CH₂—CH(OC₂H₅)(OC₂H₅) | $n_D^{20}$: 1.4870 |
| 81 | S | CH₃ | —N(3-methylpiperidine) | ¹H-NMR*: 4.6–4.9 (m) 3.5–4.1 (m) |
| 82 | S | CH₃ | x—saccharin-N-morpholine | ¹H-NMR*: 4.6–4.9 (m) 4.05–4.1 (m) 3.05–3.8 (m) |
| 83 | S | CH₃ | x—saccharin-N-piperidine | ¹H-NMR*: 4.6–4.9 (m) 3.6–4.05 (m) |

-continued
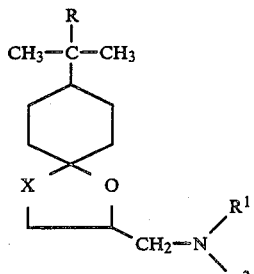  (I)
| Example No. | X | R | —N(R¹)(R²) | Physical Properties |
|---|---|---|---|---|
| 84 | S | CH₃ | [benzisothiazolinone-3-one 1,1-dioxide]; —NH—CH₂—CH(C₂H₅)(C₂H₅) | $^1$H-NMR*: 4.6–4.8 (m) 3.5–37.7 (m) 3.1–3.3 (m) 2.7–2.9 (m) |
| 85 | S | CH₃ | —NH—cyclohexyl (H) | $^1$H-NMR*: 4.6–4.8 (m) 3.1–3.6 (m) 2.7–2.9 (m) |
| 86 | S | CH₃ | [benzisothiazolinone-3-one 1,1-dioxide]; —NH—CH₂—cyclohexyl (H) | $^1$H-NMR*: 4.6–4.8 (m) 3.5–3.7 (m) 3.0–3.3 (m) 2.7–2.9 (m) |
| 87 | S | CH₃ | —NH—CH₂—CH(OC₂H₅)(OC₂H₅) | $^1$H-NMR*: 4.95–5.05 (m) 4.6–4.8 (m) 3.5–3.9 (m) 3.1–3.5 (m) |
| 88 | S | C₂H₅ | 3-methylpiperidin-1-yl | $n_D^{20}$: 1.5058 |

-continued
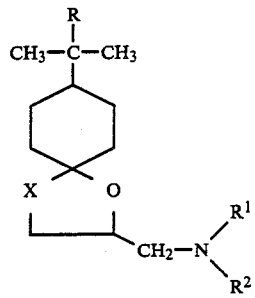
(I)
| Example No. | X | R | —N(R¹)(R²) | Physical Properties |
|---|---|---|---|---|
| 89 | S | $C_2H_5$ | (3,5-dimethylpiperidin-1-yl) | $n_D^{20}$: 1.5027 |
| 90 | S | $C_2H_5$ | (2,6-dimethylmorpholin-4-yl) | $n_D^{20}$: 1.5027 |
| 91 | S | $C_2H_5$ | —N((CH$_2$)$_2$—CH$_3$)(CH$_2$-tetrahydrofuran-2-yl) | $n_D^{20}$: 1.5027 |
| 92 | S | $C_2H_5$ | —NH—CH$_2$—CH(OC$_2$H$_5$)$_2$ | $n_D^{20}$: 1.4906 |
| 93 | S | $C_2H_5$ | —NH—(CH$_2$)$_3$—OC$_2$H$_5$ | $n_D^{20}$: 1.4969 |
| 94 | S | $C_2H_5$ | —NH—CH$_2$—cyclohexyl | $n_D^{20}$: 1.5099 |
| 95 | S | $C_2H_5$ | —NH—CH$_2$—CH(C$_2$H$_5$)$_2$ | $n_D^{20}$: 1.4958 |
| 96 | S | $C_2H_5$ | (3-methylpiperidin-1-yl) | ¹H-NMR*: = 4.6–4.9 (m) 3.5–4.0(m) |
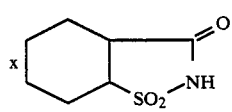

-continued
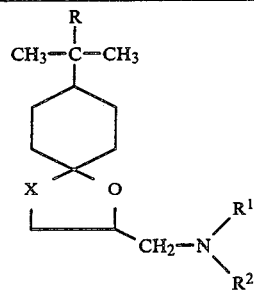
| Example No. | X | R | —N(R¹)(R²) | Physical Properties |
|---|---|---|---|---|
| 97 | S | $C_2H_5$ |  | ¹H-NMR*: = 4.6–4.9 3.5–3.9 |
| | | | 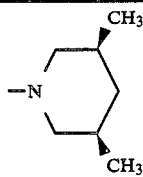 | |
| 98 | S | $C_2H_5$ | 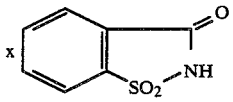 | ¹H-NMR*: 4.6–4.9 (m); 4.1–4.3 (m); 3.5–3.9 (m); 3.0–3.25 (m). |
| | | | 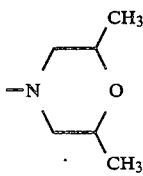 | |
| 99 | S | $C_2H_5$ | 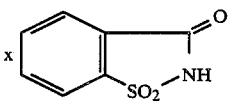 | ¹H-NMR*: 4.6–4.9 (m) 4.3–4.5 (m) 3.1–3.9 (m) |
| | | | 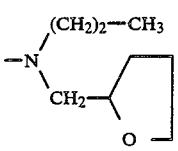 | |
| 100 | S | $C_2H_5$ | 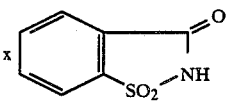 | ¹H-NMR*: 3.15–3.9 (m); 4.6–4.8 (m); 4.95–5.05 (m); |
| | | | 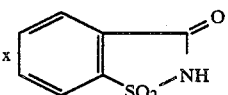 | |
| 101 | S | $C_2H_5$ | —NH—(CH₂)₃—O—C₂H₅ | ¹H-NMR*: 4.6–4.8 (m); 3.1–3.7 (m) |
| | | | 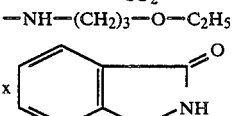 | |

-continued
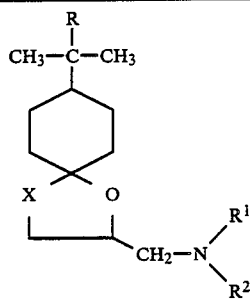
(I)
| Example No. | X | R | −N(R¹)(R²) | Physical Properties |
|---|---|---|---|---|
| 102 | S | $C_2H_5$ | −NH−CH₂−(cyclohexyl) | ¹H-NMR*: 4.5–4.8 (m); 3.5–3.75 (m); 3.0–3.25 (m); 2.7–2.9 (m); |
| 103 | S | $C_2H_5$ | −NH−CH₂−CH($C_2H_5$)($C_2H_5$) | ¹H-NMR*: 4.6–4.8 (m); 3.5–3.75 (m); 3.1–3.3 (m). |
| 104 | O | $C_2H_5$ | −N((CH₂)₂−CH₃)(CH₂-tetrahydrofuran-2-yl) | $n_D^{20}$: 1.4802 |
| 105 | O | H | −N(3,5-dimethylpiperidin-1-yl) | $n_D^{20}$: 1.4759 |
| 106 | O | H | −N(2,6-dimethylmorpholin-4-yl) | $n_D^{20}$: 1.4750 |
| 107 | O | H | −N((CH₂)₂−CH₃)(CH₂-tetrahydrofuran-2-yl) | $n_D^{20}$: 1.4760 |
| 108 | O | H | −NH−CH₂−CH($C_2H_5$)₂ | $n_D^{20}$: 1.4666 |
| 109 | O | H | −(CH₂)₃−O$C_2H_5$ | $n_D^{20}$: 1.4678 |

-continued

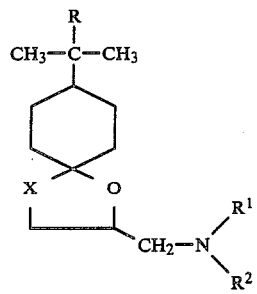
(I)

| Example No. | X | R | $-N\begin{smallmatrix}R^1\\R^2\end{smallmatrix}$ | Physical Properties |
|---|---|---|---|---|
| 110 | O | H | —NH—CH₂—(cyclohexyl) | $n_D^{20}$: 1.4836 |
| 111 | O | H | —NH—CH₂—CH(CH₃)₂ | $n_D^{20}$: 1.4643 |
| 112 | O | C₂H₅ | —N((CH₂)₂—CH₃)(CH₂-tetrahydrofuranyl) | $n_D^{20}$: 1.5226 |

| 113 | S | H | —N(3,5-dimethylpiperidinyl, trans) | $n_D^{20}$: 1.4900 |
| 114 | S | H | —N(3,5-dimethylpiperidinyl, cis) | $n_D^{20}$: 1.5000 |
| 115 | S | H | —N((CH₂)₂—CH₃)(CH₂-tetrahydrofuranyl) | $n_D^{20}$: 1.5030 |
| 116 | S | H | —NH—(CH₂)₃OC₂H₅ | $n_D^{20}$: 1.4913 |
| 117 | S | H | —NH—CH₂—CH(C₂H₅)₂ | $n_D^{20}$: 1.4910 |
| 118 | S | H | —N(3,5-dimethylpiperidinyl) | $n_D^{20}$: 1.5179 |

-continued

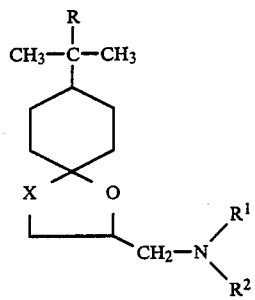

(I)

| Example No. | X | R | $-N\begin{matrix}R^1\\R^2\end{matrix}$ | Physical Properties |
|---|---|---|---|---|
| 119 | O | H | ![benzisothiazolone]—NH—(CH₂)₃—OC₂H₅ | $n_D^{20}$: 1.5058 |
| 120 | S | H | $-N\begin{matrix}(CH_2)_2-CH_3\\CH_2-\text{(tetrahydrofuryl)}\end{matrix}$ | $n_D^{20}$: 1.5260 |
| 121 | S | H | ![benzisothiazolone]—NH(CH₂)₃OC₂H₅ | $n_D^{20}$: 1.5318 |
| 122 | S | H | ![benzisothiazolone]—NH—CH₂—CH(C₂H₅)₂ | $n_D^{20}$: 1.5272 |
| 123 | O | H | —NH—(3-methylcyclohexyl, H) | $n_D^{20}$: 1.4808 |
| 124 | S | H | —NH—CH₂—(cyclohexyl, H) | $n_D^{20}$: 1.5056 |
| 125 | O | H | —NH—CH₂—(cyclohexyl, H) | ¹H—NMR*:<br>4.5–4.6 (m)<br>4.0–4.1 (m)<br>3.6–3.7 (m)<br>3.3–3.5 (m) |

-continued
(I)

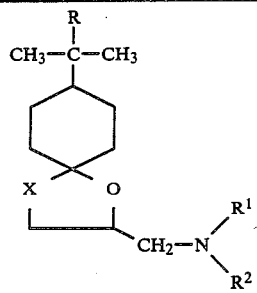

| Example No. | X | R | $-N\begin{smallmatrix}R^1\\R^2\end{smallmatrix}$ | Physical Properties |
|---|---|---|---|---|
| | | | × $CH_3-(CH_2)_{11}-C_6H_4-SO_3H$ | |
| 126 | O | $CH_3$ | $-NH-CH_2-$ (tetrahydrofuranyl) | $n_D^{20}$: 1.4812 |
| 127 | S |  | piperidinyl | $n_D^{20}$: 1.5198 |
| 128 | S | cyclohexyl-H | 3,5-dimethylpiperidinyl | $n_D^{20}$: 1.5065 |
| 129 | S | cyclohexyl-H | 2,6-dimethylmorpholinyl | $n_D^{20}$: 1.5147 |
| 130 | S | cyclohexyl-H | $-NH-CH_2-CH(C_2H_5)_2$ | $n_D^{20}$: 1.5033 |
| 131 | S | cyclohexyl-H | $-NH-CH_2-$cyclohexyl | $n_D^{20}$: 1.5186 |
| 132 | S | cyclohexyl-H | $-NH-$cyclohexyl | $n_D^{20}$: 1.5242 |
| 133 | S | cyclohexyl-H | $-NH-$(4-methylcyclohexyl) | $n_D^{20}$: 1.5189 |

-continued
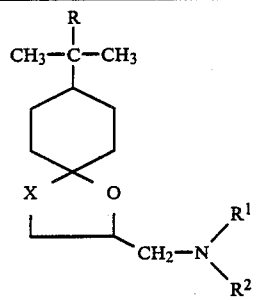
(I)
| Example No. | X | R | —N(R¹)(R²) | Physical Properties |
|---|---|---|---|---|
| 134 | S | cyclohexyl-H | piperidin-1-yl | ¹H—NMR*: 4.6–4.8 (m) 3.0–3.7 (m) |
| | | | ×—C₆H₄(o-SO₂NH—C(O)—) | |
| 135 | S | cyclohexyl-H | (3,5-dimethyl)piperidin-1-yl | ¹H—NMR*: 4.5–4.7 (m) 2.7–3.7 (m) |
| 136 | S | cyclohexyl-H | (2,6-dimethyl)morpholin-4-yl | ¹H—NMR*: 4.6–4.9 (m) 4.1–4.3 (m) 3.0–3.9 (m) |
| | | | ×—C₆H₄(o-SO₂NH—C(O)—) | |
| 137 | S | cyclohexyl-H | —NH—CH₂—CH(C₂H₅)₂ | ¹H—NMR*: 4.6–4.7 (m) 3.5–3.6 (m) 2.7–3.3 (m) |
| 138 | S | cyclohexyl-H | —NH—CH₂—cyclohexyl-H | ¹H—NMR*: 4.6–4.7 (m) 3.5–3.7 (m) 2.7–3.3 (m) |
| | | | ×—C₆H₄(o-SO₂NH—C(O)—) | |
| 139 | S | cyclohexyl-H | —NH—cyclohexyl-H | ¹H—NMR*: 4.6–4.8 (m) 3.1–3.6 (m) 2.7–2.9 (m) |

-continued

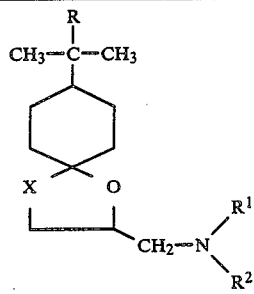
(I)

| Example No. | X | R | $-N\begin{smallmatrix}R^1\\R^2\end{smallmatrix}$ | Physical Properties |
|---|---|---|---|---|

| 140 | S | cyclohexyl-H | -NH-(3-methylcyclohexyl)-H | $^1H$—NMR*: 4.6–4.8 (m) 3.1–3.6 (m) 2.7–2.9 (m) |
| 141 | O | H | $-NH-CH_2-CH(OC_2H_5)_2$ | $n_D^{20}$: 1.4120 |
| 142 | O | $CH_3$ | $-N(CH_3)-CH_2-$(tetrahydrofuran-2-yl) | $n_D^{20}$: 1.5050 |
| 143 | O | $CH_3$ | $-N(C_2H_5)-CH_2-$(tetrahydrofuran-2-yl) | $n_D^{20}$: 1.4803 |
| 144 | O | H | piperidin-1-yl | $n_D^{20}$: 1.480 |
| 145 | O | H | 3-methylpiperidin-1-yl | $n_D^{20}$: 1.479 |
| 146 | O | H | morpholin-4-yl | $n_D^{20}$: 1.482 |
| 147 | O | $CH_3$ | piperidin-1-yl | $n_D^{20}$: 1.484 |
| 148 | O | $CH_3$ | $-NH-CH_2-$(tetrahydrofuran-2-yl) | $n_D^{20}$: 1.5221 |

-continued

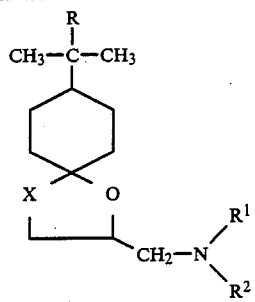
(I)

| Example No. | X | R | -N(R¹)(R²) | Physical Properties |
|---|---|---|---|---|
| 149 | O | CH₃ | -N(CH₂-C≡CH)(CH₂-tetrahydrofuran-2-yl) | $n_D^{20}$: 1.4924 |
| 150 | S | CH₃ | -NH-CH₂-(tetrahydrofuran-2-yl) | $n_D^{20}$: 1.5070 |
| 151 | S | CH₃ | -NH-(3-methylcyclohexyl) | $n_D^{20}$: 1.5030 |
| 152 | O | CH₃ | -N(CH₂-C≡CH)(3-methylcyclohexyl) | $n_D^{20}$: 1.4915 |
| 153 | S | CH₃ | -N(CH₂-C≡CH)(CH₂-tetrahydrofuran-2-yl) | $n_D^{20}$: 1.5131 |
| 154 | O | CH₃ | -NH-C(CH₃)₃ | $n_D^{20}$: 1.4686 |
| 155 | O | H | -NH-C(CH₃)₃ | $n_D^{20}$: 1.4632 |
| 156 | S | CH₃ | -N(CH₃)(CH₂-tetrahydrofuran-2-yl) | $n_D^{20}$: 1.5079 |
| 157 | S | CH₃ | -N(C₂H₅)(CH₂-tetrahydrofuran-2-yl) | $n_D^{20}$: 1.5052 |
| 158 | S | CH₃ | -NH-C(CH₃)₃ | Melting point 68°–72° C. |
| 159 | S | H | -N(piperidinyl) | $n_D^{20}$: 1.5030 |

-continued
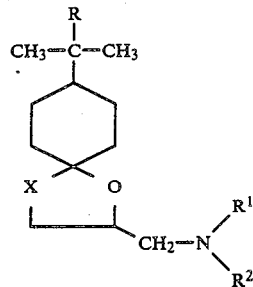
(I)
| Example No. | X | R | $-N\begin{smallmatrix}R^1\\R^2\end{smallmatrix}$ | Physical Properties |
|---|---|---|---|---|
| 160 | S | H | 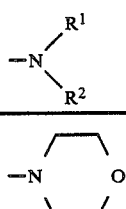 | $n_D^{20}$: 1.5081 |
| 161 | S | H | 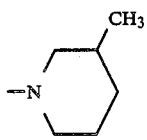 | 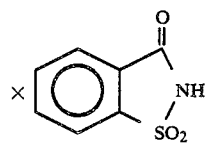 |
| 162 | S | H | 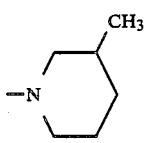 | $n_D^{20}$: 1.501 |
| 163 | S | $C_2H_5$ | 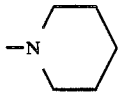 | $n_D^{20}$: 1.507 |
| 164 | S | $C_2H_5$ | 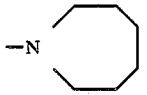 | $n_D^{20}$: 1.511 |
| 165 | S | $C_2H_5$ | 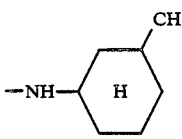 | $n_D^{20}$: 1.503 |
| 166 | S | $C_2H_5$ | 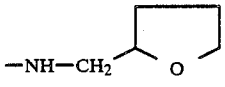 | $n_D^{20}$: 1.501 |
| 167 | O | $C_2H_5$ | 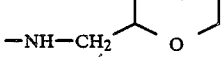 | $n_D^{20}$: 1.484 |
| 168 | S | H | 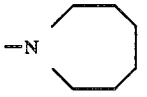 | $n_D^{20}$: 1.501 |
| 169 | O | $CH_3$ | 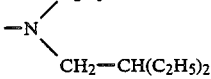 | $n_D^{20}$: 1.4674 |

-continued

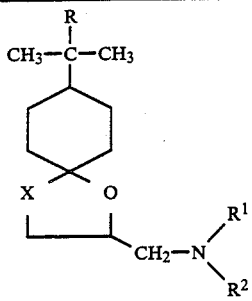

(I)

| Example No. | X | R | $-N\begin{subarray}{l}R^1\\R^2\end{subarray}$ | Physical Properties |
|---|---|---|---|---|
| 170 | O | $CH_3$ | $-N\begin{subarray}{l}(CH_2)_2-CH_3\\CH(CH_3)C_6H_5\end{subarray}$ | $n_D^{20}$: 1.5043 |
| 171 | O | $CH_3$ | $-NH-CH(CH_3)C_6H_5$ | $n_D^{20}$: 1.5088 |
| 172 | O | $-CH_2-C(CH_3)_3$ | $-NH-CH_3$ | Melting point 140° C./0.5 mbar |
| 173 | O | $-CH_2-C(CH_3)_3$ | $-NH-C_2H_5$ | Melting point 143–145° C./0.5 mbar |
| 174 | O | cyclohexyl-H | $-NH-CH_3$ | Melting point 172° C./0.9 mbar |
| 175 | O | cyclohexyl-H | $-NH-C_2H_5$ | Melting point 178° C./0.7 mbar |
| 176 | O | cyclohexyl-H | $-N\begin{subarray}{l}CH_3\\(CH_2)_2-CH_3\end{subarray}$ | $n_D^{20}$: 1.4898 |
| 177 | O | cyclohexyl-H | $-N\begin{subarray}{l}CH_3\\(CH_2)_3-CH_3\end{subarray}$ | $n_D^{20}$: 1.4893 |
| 178 | O | cyclohexyl-H | $-N\begin{subarray}{l}C_2H_5\\(CH_2)_2-CH_3\end{subarray}$ | $n_D^{20}$: 1.4885 |
| 179 | O | cyclohexyl-H | $-N\begin{subarray}{l}C_2H_5\\(CH_2)_3-CH_3\end{subarray}$ | $n_D^{20}$: 1.4874 |
| 180 | O | $-CH_2-C(CH_3)_3$ | $-N\begin{subarray}{l}CH_3\\(CH_2)_2-CH_3\end{subarray}$ | $n_D^{20}$: 1.4722 |

-continued

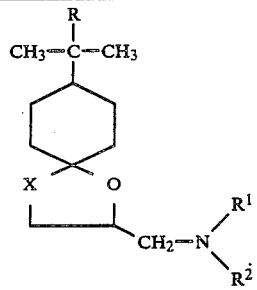

(I)

| Example No. | X | R | $-N\begin{smallmatrix}R^1\\R^2\end{smallmatrix}$ | Physical Properties |
|---|---|---|---|---|
| 181 | O | $-CH_2-C(CH_3)_3$ | $-N\begin{smallmatrix}CH_3\\(CH_2)_3-CH_3\end{smallmatrix}$ | $n_D^{20}$: 1.4728 |
| 182 | O | $-CH_2-C(CH_3)_3$ | $-N\begin{smallmatrix}C_2H_5\\(CH_2)_2-CH_3\end{smallmatrix}$ | $n_D^{20}$: 1.4732 |
| 183 | O | $-CH_2-C(CH_3)_3$ | $-N\begin{smallmatrix}C_2H_5\\(CH_2)_3-CH_3\end{smallmatrix}$ | $n_D^{20}$: 1.4726 |
| 184 | O | $CH_3$ | $-NH-(CH_2)_2-CH_3$ | $n_D^{20}$: 1.4684 |
| 185 | O | $-CH_2-C(CH_3)_3$ | 3,5-dimethylpiperidin-1-yl | $n_D^{20}$: 1.4831 (Diastereomer A) |
| 186 | O | cyclohexyl (H) | 3,5-dimethylpiperidin-1-yl | Melting point 68–70° C. (Diastereomer A) |
| 187 | O | cyclohexyl (H) | 3,5-dimethylpiperidin-1-yl | $n_D^{20}$: 1.4959 (Diastereomer B) |
| 188 | O | $CH_3$ | $-N\begin{smallmatrix}CH_2-COOC_2H_5\\CH_2-CH(C_2H_5)_2\end{smallmatrix}$ | $n_D^{20}$: 1.4668 |
| 189 | O | $CH_3$ | $-N\begin{smallmatrix}C_2H_5\\(CH_2)_3-OC_2H_5\end{smallmatrix}$ | $n_D^{20}$: 1.4656 |

Use Examples

The compounds shown below were employed as comparison substances in the use example which follows:

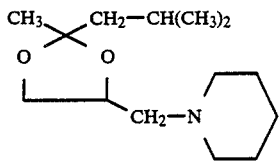

2-Isobutyl-2-methyl-4-(1-piperidinylmethyl)-1,3-dioxolane and

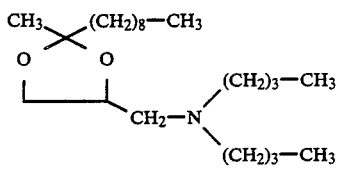

2-Methyl-2-nonyl-4-di-n-butylaminomethyl-1,3-dioxolane (both known from European Pat. No. 97,822).

Example A

Pyrenophora teres test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of Pyrenophora teres. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to preparation examples: 1, 2, 3, 4, 5, 6, 7 and 8.

It will be understood that the specification and examples are illustrative but not limitative of the present invention and that other embodiments within the spirit and scope of the invention will suggest themselves to those skilled in the art.

We claim:

1. An aminomethylheterocyclic compound of the formula

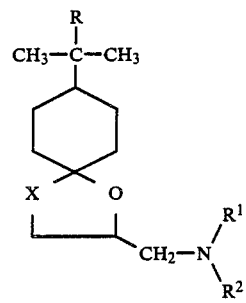

in which
X represents oxygen or sulphur,
R represents hydrogen, or represents straight-chain or branched alkyl with 1 to 6 carbon atoms, or represents phenyl or cyclohexyl, in each case unsubstituted or mono-, di- or tri-substituted by identical or different substituents selected from the group consisting of alkyl with 1 to 4 carbon atoms or halogen, and
$R^1$ and $R^2$ independently of one another each represent hydrogen; or represent in each case straight-chain or branched alkyl with 1 to 12 carbon atoms, alkenyl with 3 to 8 carbon atoms, alkinyl with 3 to 8 carbon atoms, hydroxyalkyl with 2 to 6 carbon atoms, alkoxyalkyl or dial-koxyalkyl with in each case 1 to 6 carbon atoms or hydroxyalkoxyalkyl with 2 to 6 carbon atoms in the individual alkyl parts, alkoxycarbonyl alkyl with 1 to 6 carbon atoms in the alkoxy and alkyl part, or represent in each case straight-chain or branched dioxolanylalkyl, dioxanylalkyl or oxolanylalkyl with in each case 1 to 4 carbon atoms in the alkyl part, or represent cycloalkyl or cycloalkylalkyl with in each case 3 to 7 carbon atoms in the cycloalkyl part and where appropriate 1 to 4 carbon atoms in the straight-chain or branched alkyl part and in each case unsubstituted or mono- or poly-substituted in the cycloalkyl part by identical or different substituents selected from the group consisting of halogen and in each case straight-chain or branched alkyl, alkoxy, halogenoalkyl and halogenoalkoxy with in each case 1 to 4 carbon atoms and where appropriate 1 to 9 identical or different halogen atoms; or furthermore represent arylalkyl, arylalkenyl or aryl with in each case 6 to 10 carbon atoms in the aryl part and where appropriate up to 6 carbon atoms in the straight-chain or branched alkyl or alkenyl part, in each case unsubstituted or mono- or poly-substituted in the aryl part by identical or different substituents selected from the group consisting of halogen, cyano, nitro and in each case straight-chain or branched alkyl, alkoxy, alkylthio, halogenoalkyl, halogenoalkoxy, halogenoalkylthio, alkoxycarbonyl and alkoximinoalkyl with in each case 1 to 4 carbon atoms in the individual alkyl parts and where appropriate 1 to 9 identical or different halogen atoms, or
$R^1$ and $R^2$, together with the nitrogen atom to which they are bonded, represent a heterocyclic radical of the formula

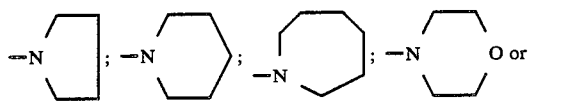

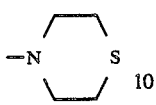

which is unsubstituted or mono- or polysubstituted by identical or different substituents selected from the group consisting of straight-chain or branched alkyl and hydroxyalkyl with in each case 1 to 4 carbon atoms, or an acid addition salt thereof.

2. An aminomethyl heterocyclic compound or salt thereof according to claim 1, in which R represents hydrogen, methyl, ethyl, neopentyl, cyclohexyl or phenyl and $R^1$ and $R^2$ independently of one another in each case represent hydrogen, methyl, ethyl, n- or i-propyl, n-, i-, s- or t-butyl, n- or i-pentyl, n- or i-hexyl, n- or i-heptyl, n- or i-octyl, allyl, n- or i-butenyl, n- or i-pentenyl, propargyl, n- or i-butinyl, hydroxyethyl, hydroxypropyl, methoxyethyl, ethoxyethyl, propoxyethyl, butoxyethyl, methoxypropyl, ethoxypropyl, propoxypropyl, butoxypropyl, hydroxyethoxyethyl, di-methoxyethyl, dimethoxypropyl, diethoxyethyl, methoxycarbonylmethyl, methoxycarbonylethyl, methoxycarbonylpropyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, dioxanylethyl, oxolanylmethyl or oxolanylethyl, or represent cyclopropyl, cyclopropylmethyl, cyclopropylethyl, cyclopropylpropyl, cyclopentyl, cyclopentylmethyl, cyclohexyl or cyclohexylmethyl, in each case unsubstituted or mono-, di-, tri-, tetra- or pentasubstituted by identical or different substituents from the group consisting of fluorine, chlorine, bromine, methyl, ethyl, n- or i-propyl and/or n-, i-, s- or t-butyl, or represent phenyl, benzyl or phenethyl, in each case optionally mono-, di- or tri-substituted by identical or different substituents selected from the group consisting of fluorine, chlorine, bromine, cyano, nitro, methyl, ethyl, n- or i-propyl, n-, i-, s- or t-butyl, methoxy, ethoxy, methylthio, trifluormethyl, trifluoromethoxy, trifluoromethylthio, methoxycarbonyl, ethoxycarbonyl and methoximinomethyl, or $R^1$ and $R^2$, together with the nitrogen atom to which they are bonded, represent a heterocyclic radical of the formula

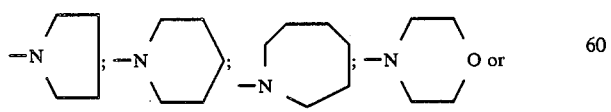

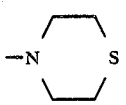

which is unsubstituted or mono-, di- or trisubstituted by identical or different substituents selected from the group consisting of methyl, ethyl and hydroxymethyl.

3. An aminomethyl heterocyclic compound or salt thereof according to claim 1, in which R represents hydrogen, methyl or ethyl and $R^1$ and $R^2$ independently of one another each, represent hydrogen, methyl, ethyl, n- or i-propyl, n-, i-, s- or t-butyl, n- or i-pentyl, n- or i-hexyl, allyl, n- or i-butenyl, n- or i-pentenyl, propargyl, n- or i-butinyl, hydroxyethyl, hydroxypropyl, methoxyethyl, methoxypropyl, ethoxyethyl, ethoxypropyl, hydroxyethoxyethyl, dimethoxyethyl, diethoxyethyl, methoxycarbonylmethyl, methoxycarbonylethyl, methoxycarbonylpropyl, ethoxycarbonylethyl, ethoxycarbonylpropyl, propoxycarbonylmethyl, propoxycarbonylethyl, propoxycarbonylpropyl, dioxolanylmethyl, dioxolanylethyl, dioxanylmethyl, oxolanylmethyl, oxolanylethyl, cyclopropylmethyl, dichlorocyclopropylmethyl, dimethylcyclopropylmethyl, dichlorodimethylcyclopropylmethyl, cyclopentyl, cyclohexyl or cyclohexylmethyl, or $R^1$ and $R^2$, together with the nitrogen atom to which they are bonded, represent a heterocyclic radical of the formula

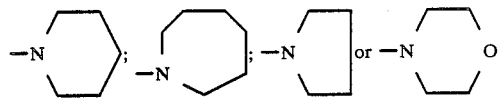

which is unsubstituted or mono-, di- or trisubstituted by identical or different substituents selected from the group consisting of methyl, ethyl and hydroxymethyl.

4. A compound according to claim 1, wherein such compound is 8-t-butyl-2-(piperidin-1-yl-methyl)-1,4-dioxaspiro[4,5]decane of the formula

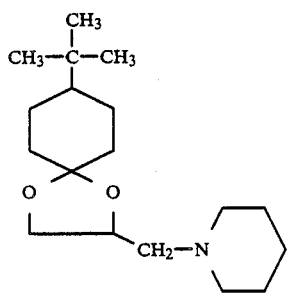

or an acid addition salt thereof.

5. A compound according to claim 1, wherein such compound is 8-t-butyl-2-(3-methyl-piperidin-1-yl-methyl)-1,4-dioxaspiro[4,5]decane of the formula

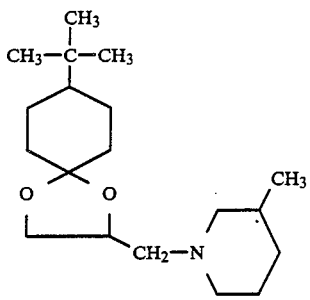

or an acid addition salt thereof.

6. A compound according to claim 1, wherein such compound is 8-t-butyl-2-(3,5-dimethyl-piperidin-1-yl-methyl)-1,4-dioxaspiro[4,5]decane of the formula

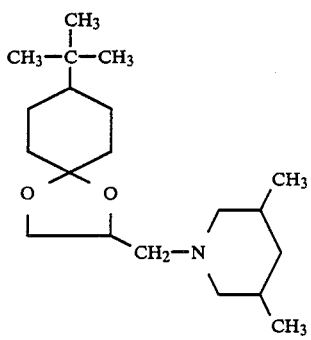

or an acid addition salt thereof.

7. The compound according to claim 1, wherein such compound is 8-t-butyl-2-(hexamethylenimin-1-yl-methyl)-1,4-dioxaspiro[4,5]decane of the formula

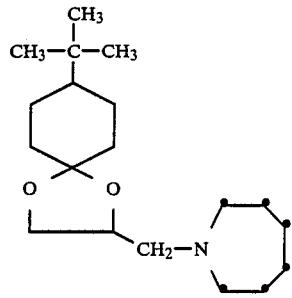

or an acid addition salt thereof.

8. A compound according to claim 1, wherein such compound is 8-t-butyl-2-(cyclohexylaminomethyl)-1,4-dioxaspiro[4,5]decane of the formula

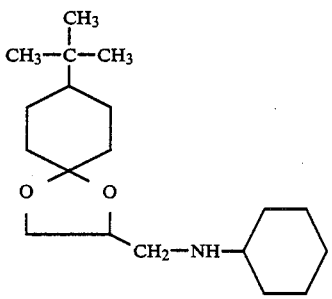

or an acid addition salt thereof.

9. A fungicidal composition comprising a fungicidally effective amount of a compound or salt according to claim 1 and a diluent.

10. A method of combating fungi which comprises applying to such fungi or to a fungus habitat a fungicidally effective amount of a compound or salt according to claim 1.

11. The method according to claim 10, wherein such compound is
8-t-butyl-2-(piperidin-1-yl-methyl)-1,4-dioxaspiro-[4,5]decane,
8-t-butyl-2-(3-methyl-piperidin-1-yl-methyl)-1,4-dioxaspiro[4,5]decane,
8-t-butyl-2-(3,5-dimethyl-piperidin-1-yl-methyl)-1,4-dioxaspiro[4,5]decane,
8-t-butyl-2-(hexamethylenimin-1-yl-methyl)-1,4-dioxaspiro[4,5]decane or
8-t-butyl-2-(cyclohexylaminomethyl)-1,4-dioxaspiro-[4,5]decane, or an acid addition salt thereof.

* * * * *

UNITED STATES PATENT AND TRADEMARK OFFICE
CERTIFICATE OF CORRECTION

PATENT NO. : 4,851,405
DATED : July 25, 1989
INVENTOR(S) : Wolfgang Krämer, et al It is certified that error appears in the above-identified patent and that said Letters Patent is hereby corrected as shown below:

| | |
|---|---|
| Title Page, line 2 and line 1 of "Inventors" | Delete "Kramer" and substitute --Krämer-- |
| Title Page, under "U.S. Patent Documents" | Line 3 delete "Bath" and substitute --Eden--; line 6 correct --Weissmüller--; line 7 correct --Krämer et al--. |
| Col. 16, line 1 | Delete "THe" and substitute --The-- |
| Col. 16, line 37 | Delete "furmaric" and substitute --fumaric-- |
| Col. 18, lines 10-11 | Correct spelling of --suitable-- |
| Col. 20, line 5 | Delete "COMPOUNDS" and substitute --COMPOUND-- |
| Col. 55, Example 140 | Underneath formula in 3rd column insert: 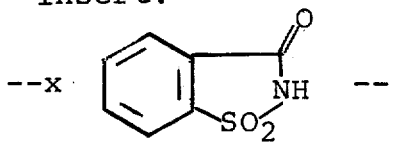 |
| Col. 66, line 30 | Correct --dialkoxyalkyl-- |
| Col. 66, line 33 | Delete "alkoxycarbonyl alkyl" and substitute --alkoxycarbonylalkyl-- |
| Col. 67, line 30 | Correct --dimethoxyethyl-- |

UNITED STATES PATENT AND TRADEMARK OFFICE
CERTIFICATE OF CORRECTION

PATENT NO. : 4,851,405

DATED : July 25, 1989

INVENTOR(S) : Woflgang Krämer, et al

It is certified that error appears in the above-identified patent and that said Letters Patent is hereby corrected as shown below:

Col. 69, line 47                    Delete "the" and substitute --A--

Signed and Sealed this

Twentieth Day of November, 1990

Attest:

HARRY F. MANBECK, JR.

*Attesting Officer*             *Commissioner of Patents and Trademarks*